United States Patent [19]

Litt et al.

[11] Patent Number: 5,084,566

[45] Date of Patent: Jan. 28, 1992

[54] DNA PROBE WHICH REVEALS A HYPERVARIABLE REGION ON HUMAN CHROMOSONE 1

[76] Inventors: Michael Litt, 3865 NE. Klickitat, Portland, Oreg. 97212; Norman E. Buroker, 21617 88th Ave. W., Edmonds, Wash. 98020

[21] Appl. No.: 593,575

[22] Filed: Oct. 5, 1990

Related U.S. Application Data

[63] Continuation of Ser. No. 46,831, May 4, 1987, abandoned.

[51] Int. Cl.⁵ .................... C12Q 1/68; C07H 21/04
[52] U.S. Cl. ........................................... 536/27; 435/6; 435/172.3; 436/501; 935/78
[58] Field of Search ............... 435/6, 172.3; 436/501; 536/27; 935/78

[56] References Cited

U.S. PATENT DOCUMENTS

| | | | |
|---|---|---|---|
| 4,302,204 | 11/1981 | Wahl et al. | 23/230.3 |
| 4,468,464 | 8/1984 | Cohen et al. | 435/317 |
| 4,594,318 | 6/1986 | Gusella et al. | 435/6 |
| 4,623,619 | 11/1986 | Owerbach et al. | 435/6 |

OTHER PUBLICATIONS

White, R. et al., (1986) in *DNA Probes, Applications in Genetic and Inf. Disease and Cancer*, (Ed. L. S. Lerman, Cold Spring Harbor Labs, Cold Spring Harbor, N. Y.) pp. 43–47.

Wyman et al., "A highly polymorphic locus in human DNA", *Proc. Natl. Acad. Sci. USA*, 77:6754–6758 (1980).

Jeffreys et al., "Individual-specific 'fingerprints' of human DNA", *Nature*, 316:76–79 (1985).

Buroker et al., "A hupervariable DNA region on human chromosome 1p", *Genetics*, 113:PT2 (Supp. 1986).

Nakamura et al., "Characterization of a human 'midisatellite' sequence", *Nucleic Acids Research*, 15:2537–2547 (1987).

*Primary Examiner*—Robert A. Wax
*Assistant Examiner*—Ardin H. Marschel
*Attorney, Agent, or Firm*—Klarquist, Sparkman, Campbell, Leigh & Whinston

[57] ABSTRACT

A DNA probe pl-79 is homologous to at least a portion of a hypervariable DNA region located at chromosome 1p36.3 in the human genome. The DNA region displays extensive restriction fragment length polymorphisms when digested with certain restriction endonucleases. Probe pl-79 is believed to have a repeated 39 base sequence CCTGGGGGTGNGNGTGCTGTTCCAGGCTG-TCAGAGGCTC, and can be used as a genetic "fingerprint" to establish human identity, determine engraftment of bone marrow transplants, determine parentage, and otherwise map genes.

25 Claims, 8 Drawing Sheets

```
Repeat #
    1) CCTGTGTGTG-TGCGCGCTGTTCCAGGCTGTCAGATGCTC
    2) CCTGGGGGTGCAGAGTGCTGTTCCAGGCTGTCAGAGGCTC
    3) ATTTCTGGTTGTGGGTGCTGCTCCTGACCATCAGATACAC
    4) CCTGGGGGTGC-GGGTGCTGCTCCAGGGTGTCGGAGGCTC
    5) CCT  GGGT  T GGT CTGTTCCAGGATATCAGCTGCTC
    6) CCTGT-GGTG-TGGGTGCTGTTCCAGGCTGTCAGAT-CTC
Consensus- CCTGGGGGTG-NGNGTGCTGTTCCAGGCTGTCAGAGGCTC
Nakemura and White- CCTGGGGGTG-TGGGTGCTGCTACGGGCTGTCAGATTCTCA
```

NUMBER OF GRAINS

DNA PROBE WHICH REVEALS A HYPERVARIABLE REGION ON HUMAN CHROMOSONE 1

The government has rights in this invention, which was funded in part by grant RO1-GM 32500 from the National Institutes of Health.

This application is a continuation of application Ser. No. 07/046,831, filed on May 4, 1987, now abandoned.

BACKGROUND OF THE INVENTION

1. Field of the Invention

The present invention concerns a restriction enzyme mapping probe for human chromosome 1.

2. General Discussion of the Background

Restriction fragment length polymorphisms (RFLP) are useful markers for mapping the human genome, Botstein, et al., *Am. J. Hum. Genet.*, 32:314-331 (1980). As the number of known RFLPs increases, they are becoming ever more useful in the prenatal or early diagnosis of numerous hereditary diseases. RFLPs are also used in mapping a diseased gene to a specific chromosomal location, which may serve as the first step in cloning the gene.

Diseases that have been mapped by linkage studies with RFLPs include Huntington's Disease, Gusella, et al., *Nature*, 306:234-238, (1983); Duchenne's muscular dystrophy, Murray, et al., *Nature*, 300:542-544, (1982); X-Linked Retinitis Pigmentosa, Bhattacharya, *Nature* 309:253-255 (1984); adult polycystic kidney disease, Reeders, et al., *Nature* 317:542-544 (1985); and cystic fibrosis, Tsui, et al., *Science* 230:1054-1056 (1985). RFLPs also have been crucial to the elucidation of mechanisms underlying hereditary cancer syndromes frequently associated with chromosome deletions such as retinoblastoma, Cavenee, *Nature* 305:779-784 (1983), and Wilm's tumor, Koufos, et al., *Nature* 309:170-172 (1984). In the future, RFLPs may be useful in characterizing the genetic contributions to susceptibility to common diseases which tend to cluster in families, such as colon cancer and schizophrenia, White, et al., Nature 313:101-105 (1985). For example, U.S. Pat. No. 4,623,619 discloses a method of using a probe to determine the liability of human individuals to develop atherosclerosis.

RFLPs can also provide individual-specific "fingerprints" of human DNA which can be used for such forensic purposes as identification of corpses, paternity testing, and identification of rapists. For example, Jeffreys, et al. disclosed in *Nature*, 316:76-79 (1985) that simple tandem-repetitive regions of DNA ("minisatellites") which are dispersed throughout the human genome frequently show substantial length polymorphism arising from unequal exchanges which alter the number of short tandem repeats in a minisatellite. The repeat elements in a subset of human minisatellites share a common 10-15 base-pair core sequence. A hybridization probe consisting of the core repeated in tandem can detect many highly polymorphic minisatellites simultaneously to provide a set of genetic markers of general use in human linkage analysis. Certain probes can detect sets of hypervariable minisatellites to produce somatically stable DNA "fingerprints" which are completely specific to an individual (or an identical twin) and can be applied directly to problems of human identification, including parenthood testing. Unfortunately, the Jeffreys, et al., probe detects repeated sequences that occur throughout the entire human genome, and give rise to very complex electrophoresis patterns that are sometimes difficult to interpret.

Hypervariable DNA regions have been reported near the human insulin gene (Bell, et al., *Nature*, 295:31-35 (1982)), in the α-globin gene cluster (Higgs, et al., *Nucleic Acids Res.*, 9:4213-4224 (1981); Proudfoot, et al., *Cell*, 31:553-563 (1982); Goodbourn, et al., *Proc. Natl. Acad. Sci. U.S.A.*, 80:5022-5026 (1983)), near the c-Ha-Ras-1 oncogene (Capon, et al., *Nature* 302:33-37 (1983)) and at the telomere of the X and Y chromosomes (Cook, et al., *Nature*, 317, 687-692 (1985)). In all cases where DNA sequence information in these regions is available, it shows that the region consists of tandemly repeated sequences which vary in copy number among chromosomes. These hypervariable regions are hypothesized to arise by mitotic or meiotic unequal crossing over or by DNA slippage during replication (Jeffreys, et al., 1985). Hypervariable regions give rise to highly polymorphic loci at numerous genomic sites. DNA probes from such regions have been useful in paternity testing and other forensic applications as well as in human gene mapping.

SUMMARY OF THE INVENTION

The present invention is a DNA probe p1-79, which is substantially homologous to at least a portion of a hypervariable DNA region located at chromosome 1p36.3 in the human genome. The DNA region displays extensive restriction fragment length polymorphisms when digested with certain restriction endonucleases. When used to probe Southern blots of TaqI-digested DNA's from unrelated individuals, p1-79 reveals at least 50 fragments, many of which are polymorphic. Similar variation is seen with several other enzymes, including HaeIII, MspI, PstI and PvuII.

DNA sequencing of p1-79 reveals several copies of a 39 bp repeat whose variation in copy number might be the basis of the observed length polymorphisms. The probe is believed to have a repeated thirty-nine base sequence CCTGGGGGTGNGNGTGCTGTTCCAGGCTGTCAGAGGCTC.

Four specific repeat sequences which fall within this more general sequence are CCTGTGTGTGTGCGCGCTGTTCCAGGCTGTCAGATGCTC; CCTGGGGGTGCAGAGTGCTGTTCCAGGCTGTCAGAGGCTC; CCTGGGGGTGCGGGTGCTGCTCCAGGGTGTCGGAGGCTC; CCTGTGGTGTGGGTGCTGTTCCAGGCTGTCAGATCTC.

The hypervariable DNA region to which probe p1-79 corresponds was identified by using a probe from a human genomic cosmid library. Cosmid 2-30 produced autoradiograms that indicated extensive DNA fragment size variation between unrelated individuals. Probe p1-79 is a 900 bp subclone of the cosmid which has been placed in a plasmid for cloning.

The present invention includes a method of producing a genetic band pattern or "fingerprint" by digesting a human genome with a restriction endonuclease which, in combination with probe p1-79, produces polymorphic fragments. The fragments are then separated by agarose gel electrophoresis, partially transferred to a nitrocellulose filter, and exposed to radioactively labeled p1-79. The labeled probe hybridizes to fragments of DNA on the filter having homologous sequences.

Autoradiographs produce a distinct band pattern which is used in human gene linkage analysis.

Probe p1-79 produces distinct band patterns which are characteristic of the individual from which the genome was taken. The band pattern can therefore be used for such forensic purposes as establishing the identity of a disfigured corpse or an accused assailant in a rape case. Medical applications include determining engraftment of bone marrow transplants, where it is helpful to determine if the marrow propagating in a patient's bone is diseased original tissue or healthy graft tissue. The probe can also be used to determine parentage because band patterns produced by the probes are inherited in a simple Mendelian fashion. Probe p1-79 is also useful in mapping genes because the probe marks a specific region close to the telomere of the short arm of human chromosome 1.

The foregoing and other objects, features, and advantages of the invention will become more apparent from the following detailed description of a preferred embodiment which proceeds with reference to the accompanying drawings.

DETAILED DESCRIPTION OF PREFERRED EMBODIMENT

For the construction of linkage maps of human chromosomes, marker loci with multiple alleles and a polymorphism information content (PIC) near one are very useful Botstein, et al., *Am. J. Human Genet.*, 32:314-331 (1980). Although several hundred RFLPs have been reported to date, only about 10 percent have PIC values greater than 0.5. Willard, et al., *Cytogenet. Cell Genet.*, 40:360-490 (1985). The present inventors have addressed this problem of RFLP's having low PICs by using a method for rapidly screening cosmids and other repeat-containing DNA clones to identify those with inserts homologous to genomic regions especially rich in RFLPs. Litt and White, *Proc. Nat'l. Acad. Sci. U.S.A.*, 82:6206-6210 (1985).

Radioactively labeled probes were prehybridized with a vast excess of nonradioactive total human DNA under conditions which drive repetitive (but not single copy) DNA into duplex form. These probes were used directly on Southern blots of restricted DNAs from panels of unrelated individuals to visualize low and single copy bands. Probes that displayed multiple polymorphisms by this method were further studied to obtain single copy subclones which revealed RFLPs. The inventors have successfully used these methods to characterize a highly polymorphic loci on chromosome 1 and isolate probe p1-79 which is homologous to that region. A detailed description of these methods can be found in Litt and White, *Proc. Nat. Acad. Sci. U.S.A.*, 82:6206-6210 (1985); Bufton, et al., 19 *Am. J. Human Genet.*, 38:447-460; Bufton, et al., *Hum. Genet.*, 74:425-431 (1986); Buroker, et al., *Hum. Genet.*, 72:86-94 (1986); Buroker, et al., *Hum. Genet.*, 73:340-345 (1986); Bufton, et al., *Hum. Genet.*, 76:90-95 (1987).

Subclone (p1-79), which was isolated from a random human cosmid using these methods, reveals numerous insertion/deletion polymorphisms. Although the polymorphisms revealed by this probe resemble in some respects the "minisatellite" regions reported by Jefferys, et al. (1985), they differ from minisatellites in that the sequences homologous to the probe are not dispersed throughout the genome but are tightly clustered in a specific chromosomal region, band p36.3 of human chromosome 1. DNA sequencing of p1-79 reveals several copies of a 39 bp repeat whose variation in copy number might be the basis of the observed length polymorphisms. Family studies in 3-generation Utah kindreds suggest that recombination within the hypervariable region may be sufficiently rare to allow this set of highly polymorphic loci to be treated as a single compound locus which may be useful in construction of a linkage map of the short arm of chromosome 1 and in mapping genes located therein. The designation D1Z2 has been assigned to this compound locus by the Howard Hughes Medical Institute Human Gene Mapping Library.

Methods of Preparing Cosmid and Subclones

Human DNA isolation, cosmid preparation and screening, subcloning, restriction mapping and hybridization procedures, somatic cell hybrid panels and in situ hybridization methods have been described in Litt and White, 1985; Bufton, et al., 1986; Buroker, et al., 1986; Litt, et al., 1986; and Bufton, et al., 1987. Southern blots used in this study were hybridized at 45°-47° and given a final wash in 0.1×SSC, 0.1% SDS at 65°. The somatic cell hybrid panel used in these studies has been previously described in Bufton, et al., 1986; Buroker, et al., 1986; and Litt, et al., 1986. DNAs from 3-generation Utah families were extracted from lymphoblast cell lines obtained from the Institute for Medical Research, Camden, N.J. DNA sequencing was performed using the dideoxy method of Sanger, et al., *Proc. Nat. Acad. Sci. U.S.A.*, 74:5463-5467 (1977). Small regions of the p1-79 plasmid insert were subcloned into either M13 mp8,9,18, or 19 and sequenced as described by Messing (1983). Compilation of the sequence information and alignment of the homologous regions was performed using the BIONET computer resource for molecular biology (1986). DNA homology matrix analysis (Maizel and Lenk, *Proc. Nat. Acad. Sci. U.S.A.*, 88:7665–7669 (1981)) was conducted on a Macintosh microcomputer with the microcomputer program DNA Inspector II (Gross, *Nucl. Acids Res.*, 14:591–595 (1986)).

Preparation and Characterization of RFLPs

Figure 1:
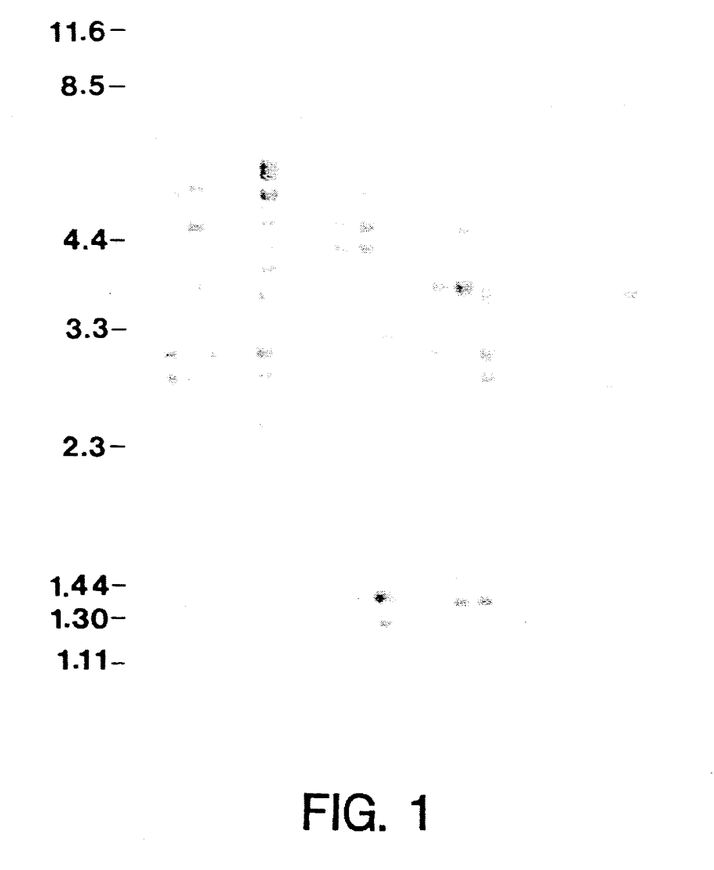
FIG. 1 shows Southern transfers of TaqI digests of DNAs from 18 unrelated individuals probed with plasmid p1-79, size markers being shown in the 11th lane from the right.

Cosmid 2-30 was found during the course of screening random human cosmids for their ability to reveal TaqI or MspI polymorphisms. The cosmid was then used as a probe after prehybridization with a vast excess of human genomic DNA (Litt and White, 1985), and revealed multiple polymorphisms with both enzymes. Similar extensive variation was observed when the cosmid was used to probe Southern blots of DNAs digested with PstI, PvuII, RsaI and HaeIII, which suggests that the polymorphisms were due to insertion/deletion events rather than to single-base changes affecting restriction sites. A Sau 3A digest of cosmid 2-30 was subcloned into the BamHI site of pSP65 and subclones which failed to hybridize with total human DNA were screened for their ability to reveal RFLPs. Thirty different subclones were tested with insert sizes varying from 0.5 to 1.6 kb as probes vs. TaqI digested DNAs; 21 of these subclones gave identical band patterns, indicating the presence of a repeated sequence. An example of the band patterns is shown in FIG. 1, which illustrates a TaqI blot of DNAs from 18 unrelated individuals probed with subclone p1-79. This subclone, with a 900 bp insert, was selected for further studies.

Figure 2:
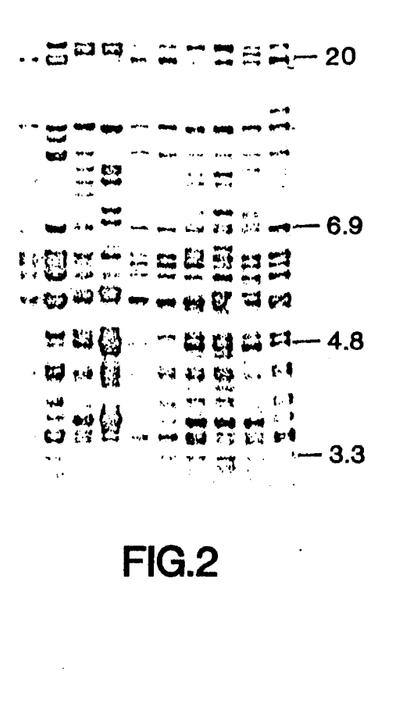
FIG. 2 shows Southern transfers of TaqI digests of DNAs from ten unrelated individuals probed with plasmid p1-79, the gel used to make this blot having been run twice as long as that used to make the blot of FIG. 1.

As shown in FIG. 1, p1-79 reveals at least 30 fragments which are larger than the 900 bp insert in the probe. Numerous polymorphisms are apparent, and the number of such polymorphisms as well as the total number of bands detected increases even further if gels are run for longer periods to improve the resolution between closely spaced bands. The gel shown in FIG. 1 was run for 24 hours and shows less resolution than a TaqI digest of the same genome run for 48 hours, which is shown in FIG. 2. The gel should preferably be run for 8 hours to produce a degree of resolution that facilitates interpretation of the band patterns.

In a survey of 27 unrelated individuals, no two identical patterns of TaqI fragments were found. Probe p1-79 hybridizes with unusually high efficiency. Thus, TaqI blots probed with p1-79 (such as those in FIGS. 1 and 2) were autoradiographed overnight without intensifying screens.

Figure 3:
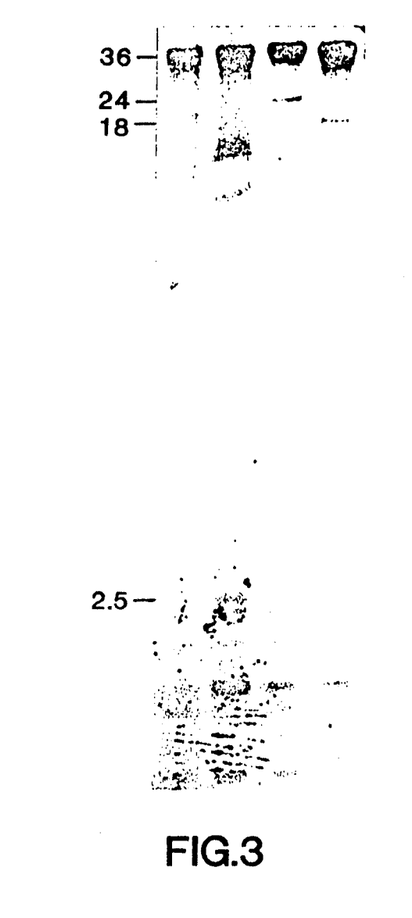
FIG. 3 shows Southern transfers of EcoRl digests of DNAs from four unrelated individuals probed with plasmid p1-79.

FIG. 3 shows a Southern blot made with EcoRI digested DNA from four unrelated individuals and probed with p1-79. The figure shows intense hybridization to a fragment of size greater than 36 kb, the largest fragment present in the size markers used on this blot. In addition to this high molecular weight band present in all individuals, a set of smaller bands is also observed. Although a few polymorphic bands appear in some individuals, the number of polymorphic bands seen on EcoRI blots is far less than seen on blots made with enzymes such as TaqI or PstI. Taken together, these results suggest that many, if not all, of the numerous loci revealed with TaqI blots are tightly clustered in a few regions which lack EcoRI sites. BglII and HindIII digests (not shown) gave results similar to those found with EcoRI.

After autoradiography, a TaqI blot probed with p1-79 was washed at high stringency (0.1×SSC/0.1% SDS at 72°), such that approximately 90% of the probe was removed. By visual inspection, the relative intensities of the bands seen on autoradiography of the rewashed blot were similar to those seen on the original autoradiograph (not shown), suggesting a similar degree of homology between the probe and most, if not all, of the numerous loci of hybridization.

Family Studies

Figure 4:
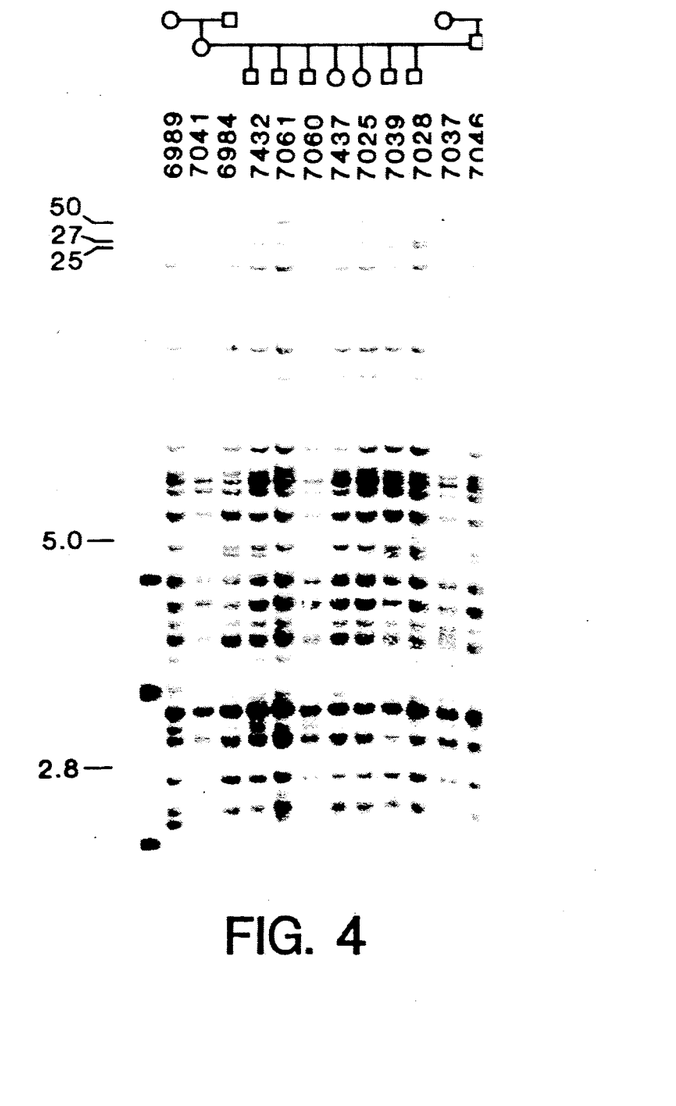
FIG. 4 shows Southern transfers of TaqI digests of DNAs from kindred K-1329C probed with plasmid p1-79, sizes of fragments whose grandparental origin can be uniquely assigned being shown along the left.

Southern blots of TaqI-digested DNAs from nine 3-generation Utah families with 6–8 children were probed with p1-79. An autoradiograph of one such blot made with family K-1329C is shown in FIG. 4. For each individual, approximately 30 bands with sizes greater than 2 kb are present. All bands show Mendelian inheritance. Three distinguishable sets of restriction fragments are seen in the seven children in this family, with three of the children (7061, 7437 and 7025) displaying identical sets of fragments. Furthermore, the grandparental origin of certain bands may be unequivocally assigned. Thus, the 50 kb bands seen in children 7061, 7437 and 7025 uniquely mark the chromosome transmitted by the paternal grandfather 7435; the 25, 5.0 and 2.8 kb bands seen in children 7432, 7060, 7039 and 7028 mark the chromosome transmitted by the paternal grandmother 7037.

In none of the other eight Utah families examined did the children display more than four different band patterns (not shown). In seven of these families, the grandparental origin of at least one TaqI restriction fragment could be uniquely assigned. In 28 children of families in which two or more such bands could be assigned to the same grandparental chromosome, it was possible to test for recombination between the loci corresponding to these bands. In the nine Utah families, none of the 28 children were recombinant for such pairs.

The DNA fingerprints produced by probe p1-79 are sufficiently stable and individual-specific for use in human identification in, for example, forensic medicine. Badly disfigured corpses can be identified by preparing a genetic fingerprint with probe p1-79, and comparing the fingerprint to bands produced by DNA of a previously collected tissue sample from a known individual who is believed to be the corpse. If the band patterns match, identity has probably been established. Rapists can similarly be identified by comparing the band patterns from semen in the victim with the band patterns produced by the DNA of an individual suspected of committing the crime.

The simple Mendelian inheritance of band patterns produced by p1-79 makes it possible to use the probe in determining parentage, for example, in a disputed paternity suit. Approximately half of the polymorphic fragments in an offspring are derived from the father, and these paternal fragments can be identified by comparison of the mother's and offspring's DNA band patterns. All fragments present in the offspring but not in the mother must be present in the father (allowing for a possible rare new mutation). The probe produces at least 50 fragments, many of which are polymorphic. The large number of polymorphic fragments makes it possible not only to exclude paternity, if bands are present in the offspring but not the mother or putative father, but also to predict statistically the possibility of inclusion of paternity. The large number of polymorphic fragments produced by the probe provides a high statistical likelihood of inclusion of paternity.

Restriction Enzyme Mapping

Probe p1-79 can also be used to map genes on chromosomes using the techniques disclosed by Gusella, et al. (1983), Murray, et al. (1982), Bhattacharya, et al. (1984), Reeders, et al. (1985) or Tsui, et al. (1985). A disease gene can be located by using the knowledge that a RFLP closely linked to a gene would be inherited with that gene. The inheritance of numerous RFLPs in families having the disease can be traced using random cloned DNA fragments from a human gene library as probes. An RFLP which is found to be inherited along with the disease indicates that the RFLP and disease gene are closely linked. Probe p1-79 will therefore indicate the presence of a disease gene close to the telomere of the short arm of human chromosome 1.

DNA Sequence

Figure 5:
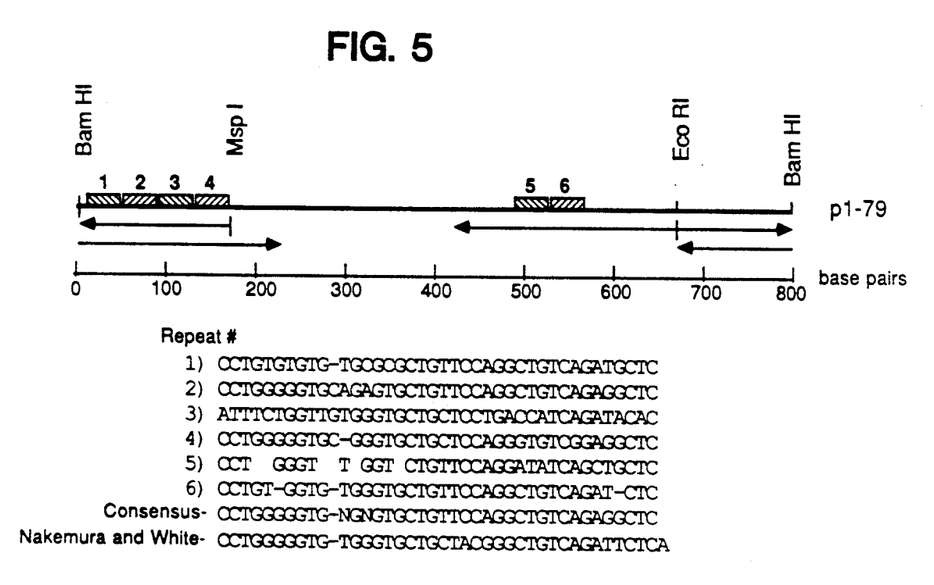
FIG. 5 shows a restriction map and repeat sequences within the p1-79 probe, arrows indicating the regions of the probe that were sequenced and the individual clones that were used.
Figure 6:
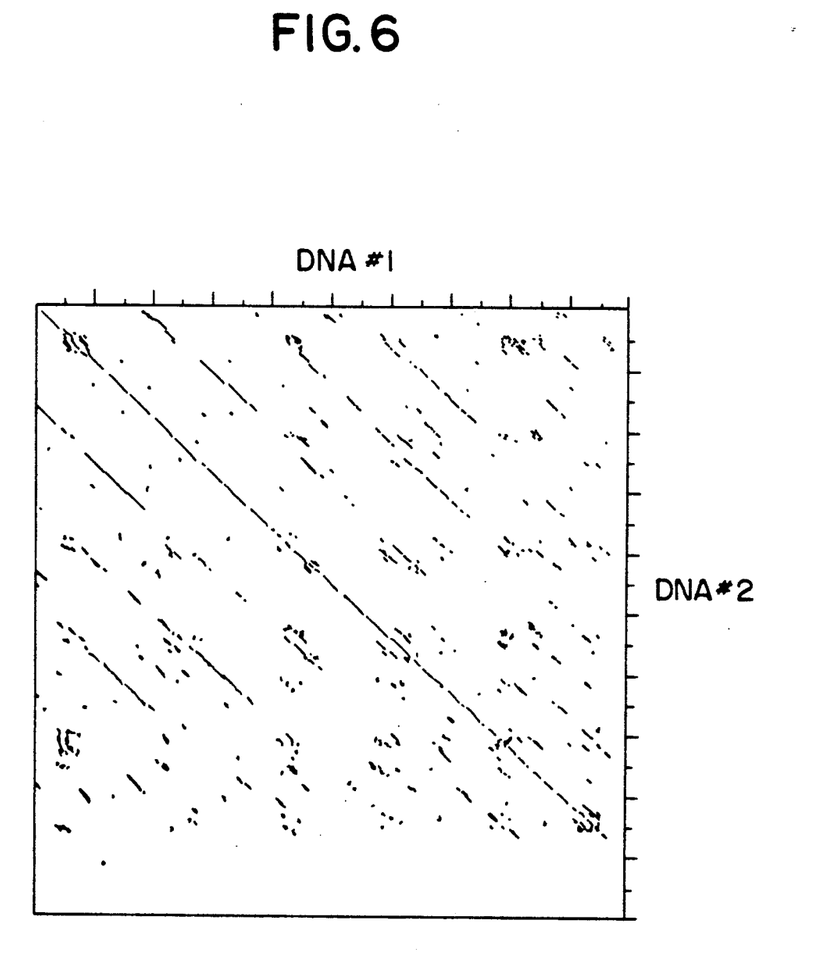
FIG. 6 shows an homology matrix analysis of p1-79 DNA sequence information, the region shown being the 225 bp BamHI-MspI fragment.

DNA sequence analysis on two regions of the p1-79 plasmid was conducted as shown in FIG. 5. Fragments from the p1-79 insert were subcloned into M13 vectors and sequenced using the dideoxynucleotide termination method (Messing, *Meth. Enz.*, 101:20-78 (1983)). DNA homology matrix analysis was conducted on both of the sequenced regions. The results from one of these analyses using the sequence of the 225 bp BamHI-MspI fragment of the p1-79 insert is shown in FIG. 6. This matrix analysis was conducted using a search element length of 8 and scoring greater than 75% homology.

The presence of a tandem 39 base pair repeating element is clearly evident as indicated by the lines of homology parallel to the main line of homology. The lines of homology have a 39 nucleotide spacing indicating that the repeat unit is 39 base pairs in length. Using the same DNA homology matrix analysis parameters, the 39 bp repeating element was also found to be present in the 3' sequenced region of p1-79 (data not shown).

FIG. 5 shows the sequences of four of these repeating elements and their locations in the p1-79 insert. All four elements have greater than 64% homology to a consensus sequence of CCTGGGGGTGNGNGTGCTGTTCCAGGCTG-TCAGAGGCTC where N indicates any nucleotide and "-" indicates a deletion or gap. Some internal regions of the repeat have much higher homology than 64%. Also shown in FIG. 5 is the repeat element present in the YN110 cosmid clone of Nakamura and White, *Nucleic Acids Res.*, 15:2537-2547 (1987). There is 85% homology between the present inventors' consensus repeat and the one discovered independently by these workers.

There are additional repeat sequences within the sequenced regions that are not shown in FIG. 5. There are no repeat units to the right of the Eco Rl site. The hatched boxes denote individual 39 base pair repeats and the numbers above each box are used to reference the listed sequences.

Using the BIONET computer system (Smith, et al., 1986), a search of the GenBank nucleic acid database was conducted using the consensus sequence shown in FIG. 5. No homologous nucleic acid sequences were found. A search for regions of dyad symmetry using homology matrix analysis and the SEQ program on BIONET revealed no regions that could form hairpin-like structures.

The present invention includes DNA probes which contain a sequence substantially homologous to the 39 base pair sequence set forth above. A substantially homologous sequence is one in which a high degree of homology between the sequences of two or more DNA molecules can be tested for by determining whether the DNA molecules in question hybridize to each other under stringent conditions, such as those set forth in Bethesda Research Laboratories, *DNA Detection System Instruction Manual* (Catalogue No. 8239SA), pp. 8-9 (1984). See also Leary et al., *Proc. Natl. Acad. Sci. U.S.A.*, 80:4045-4049 (1983), modifying the procedures of Wahl, et al., *Proc. Natl. Acad. Sci. U.S.A.*, 76:3683-3687 (1979).

Chromosomal Localization

Figure 7:
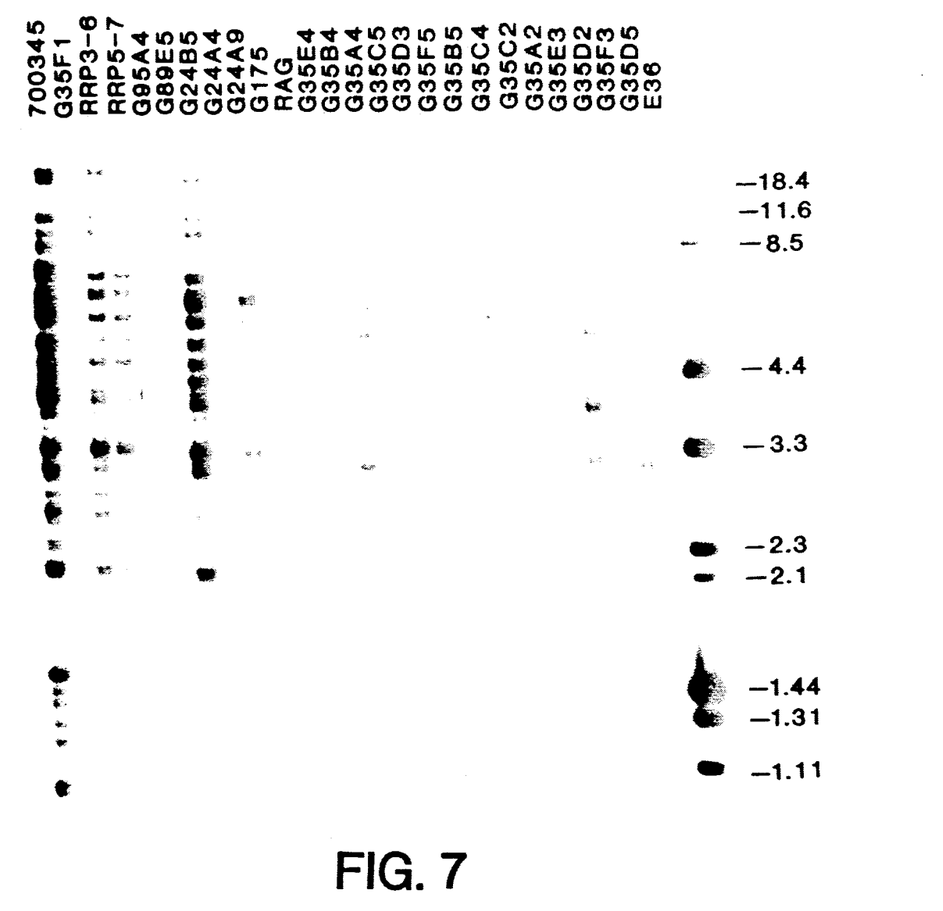
FIG. 7 shows Southern transfers of TaqI digests of DNA from parental and hybrid cell lines probed with subclone p1-79 where E36 is the hamster parent, RAG is the mouse parent and 700345 is human genomic DNA from a randomly chosen individual. The rightmost lane contains size markers, with their fragment lengths (kb) shown on the right.

When Southern transfers of TaqI-digested DNAs from a rodent-human somatic cell hybrid panel were probed with p1-79, hybridization was observed only with DNA from cell lines containing the short arm of human chromosome 1 (FIG. 7, Table 1). Similar results (not shown) were obtained with EcoRI blots of the hybrid panel DNAs, with all fragments showing concordance with chromosome 1.

TABLE 1

| Cell Line | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y | M Scoring |
|---|---|---|---|---|---|---|---|---|---|---|---|---|---|---|---|---|---|---|---|---|---|---|---|---|---|
| G35D5 | + | + | + | − | − | + | + | − | − | + | − | − | + | + | + | + | + | + | + | + | − | + | a | − | + |
| G35F3 | + | + | + | − | + | − | + | − | − | + | + | + | − | − | + | + | − | + | + | + | − | − | a | − | − |
| G35D2 | ± | − | − | − | + | + | − | − | ± | − | + | + | − | − | − | − | − | + | + | + | + | + | aR | − | + |
| G35E3 | − | − | − | ± | + | + | − | + | − | − | + | + | − | − | − | + | − | + | + | + | + | + | + | − | − |
| G35A2 | − | − | + | + | − | − | − | − | − | − | + | − | − | + | − | − | − | − | − | − | + | − | a | − | − |
| G35C2 | − | − | + | − | − | + | + | + | R | − | R | − | − | + | − | + | + | + | R | + | + | − | R | − | − |
| G35C4 | − | − | − | − | − | + | − | − | + | − | + | + | + | + | + | + | + | − | + | + | + | − | a | − | − |
| G35B5 | ± | − | + | − | − | + | − | + | + | − | + | − | + | + | + | + | + | − | + | + | + | + | + | − | − |
| G35F5 | − | P | + | − | − | R | + | + | + | ± | + | P | + | ± | + | + | + | ± | + | ± | + | + | a | − | − |
| G35D3 | − | − | − | − | − | + | − | + | + | + | + | − | − | + | + | + | ± | + | + | + | + | − | + | − | − |
| G35C5 | + | − | − | − | − | − | − | + | + | + | − | P | − | + | + | − | + | + | + | + | + | + | a | − | + |
| G35A4 | + | − | + | + | + | + | − | + | + | + | − | + | + | + | + | + | + | − | + | + | + | + | a | − | + |
| G35B4 | ± | − | − | R | + | + | − | + | R | + | + | + | + | + | + | + | + | − | + | + | + | + | a | − | − |
| G35E4 | − | − | − | + | + | + | + | + | + | + | − | + | + | + | + | + | + | + | + | + | + | + | a | − | − |
| G175 | ± | − | − | − | − | − | − | − | − | − | − | − | − | − | − | − | − | − | − | − | − | − | + | − | + |
| G24A9[b] | P | − | − | − | − | − | − | − | − | − | − | − | − | − | − | − | − | − | − | − | − | − | a | − | + |
| G24A4 | + | P | − | R | − | − | − | − | + | + | ± | − | ± | + | + | − | ± | + | − | − | + | + | q | − | + |
| G24B5 | + | P | − | + | − | − | − | − | ± | + | + | − | + | + | + | − | − | + | − | ± | + | + | q | − | + |
| G89E5[c] | − | − | − | + | − | + | + | − | − | − | − | − | + | − | − | − | − | + | − | − | + | − | + | − | + |
| G95A4 | − | − | + | + | + | + | + | − | − | + | − | − | + | + | − | − | + | + | + | + | + | − | + | − | + |
| RRP5-7 | + | + | + | + | + | + | + | − | − | + | − | + | ND | − | − | − | + | + | − | ± | − | − | + | − | + |
| RRP3-6B1 | + | − | − | − | + | + | + | − | − | ± | + | + | − | + | − | − | + | + | R | + | + | − | R | R | + |
| G35F1 | − | − | − | + | + | − | − | + | − | ± | − | P | − | + | − | − | − | + | + | + | + | − | a | + | − |
| Discordancy Fraction | 0/18 | 6/21 | 8/22 | 6/20 | 11/23 | 10/22 | 8/23 | 11/23 | 8/19 | 6/20 | 11/21 | 9/20 | 6/21 | 8/22 | 5/23 | 10/23 | 9/22 | 8/22 | 12/20 | 13/21 | 11/23 | 11/23 | 5/8 | 7/22 | |

Explanation of Table 1

Table 1 shows chromosome contents of hybrid cell lines. The designations are: (+) presence of and (−) absence of a human chromosome; (R), rearranged chromosome as determined by disruption of a syntenic group or by a cytogenetic abnormality; (±), chromosome present in less than 15% of cells and/or the isozyme or DNA probe characteristic of the chromosome weakly positive; (p), presence of a marker for the short arm and absence of a marker for the long arm; (q), presence of a marker for the long arm and absence of a marker for the short arm; (a) Xq24→qter.

For calculation of the discordancy fractions, hybrids with a rearranged chromosome or those where the chromosome was present in less than 15% of the cells were excluded from analysis. The column designated M indicates the presence or absence of human-specific TaqI or EcoRI fragments in Southern transfers probed with subclone p1-79. Cell line G24A9[b] hybridizes with a U1SnRNA pseudogene, previously localized to 1p36(23), but lacks other chromosome 1 specific loci. [c]Cell line G89E5 contains an X chromosome in all cells plus an unidentified human-hamster translocation in about 20% of the cells.

In Situ Hybridization

In situ hybridization of p1-79 (FIGS. 8 and 9) showed localization to 1p36.3, with 86% of the cells having a silver grain localized to this region.

Figure 8A:
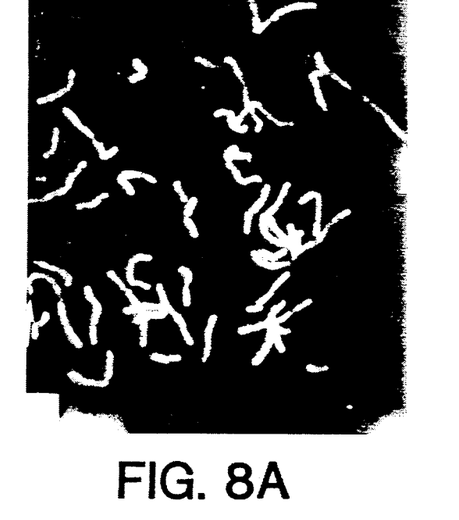
FIG. 8 shows in situ hybridization of probe p1-79 to a metaphase spread from a normal male.
Figure 8B:
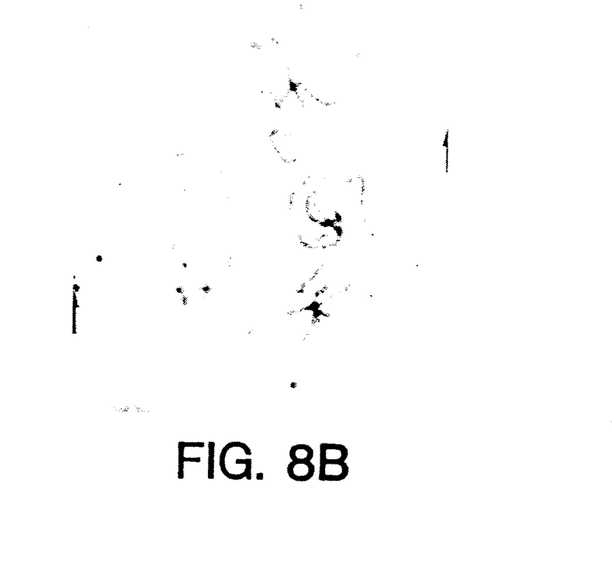

On the left of FIG. 8 is a representative metaphase that has been R-banded following hybridization. On the right of FIG. 8 is the same metaphase, destained and restained with Wright's stain to show silver grains. Arrows indicate silver grains over 1p36.3 and the corresponding locations in the R-banded metaphase.

Figure 9:
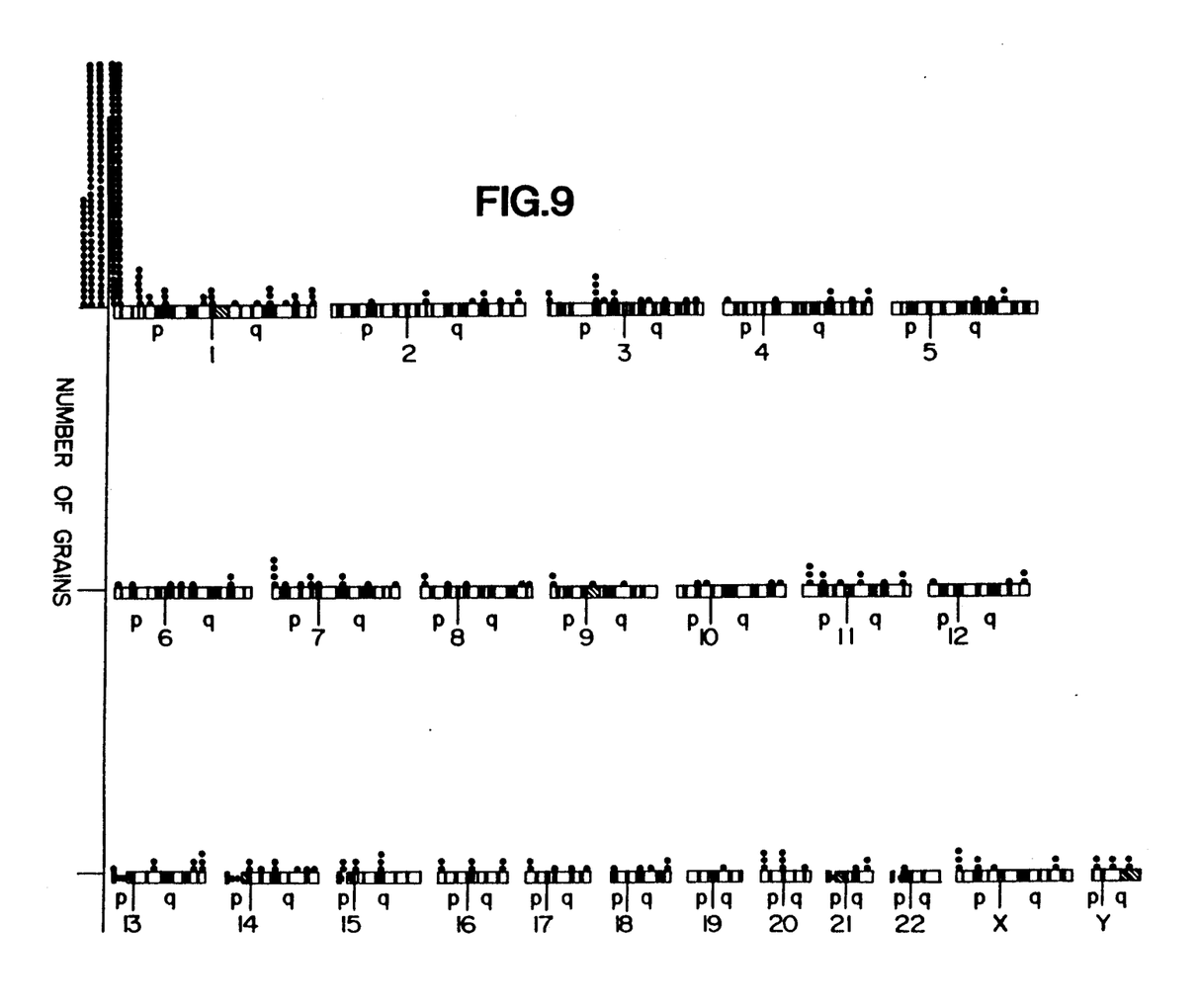
FIG. 9 shows a histogram of chromosomal distribution of silver grains from in situ hybridization of probe p1-79 to chromosomes of a normal male.

Each dot in FIG. 9 represents a grain observed over a specific chromosomal region. Out of 100 cells examined, 86 had a grain localized over 1p36.3. The rest of the label was randomly distributed over the chromosomes.

Hypervariable region D1Z2 is detected by the 900 bp probe p1-79 and localized to band p36.3 of human chromosome 1. Although not desiring to be bound by theory, the present inventors believe that variations in the copy number of a repeated sequence may be responsible for the extensive polymorphism revealed by p1-79, as has been found in the case of minisatellites (Jeffreys, et al., 1985). Indeed, DNA sequencing of p1-79 revealed seven copies of a tandemly repeated 39 bp sequence, four of which were greater than 70% homologous to a consensus sequence. Since the blots used in this study were hybridized and washed at high stringency, it seems likely that the hybridizing fragments contain a more highly conserved higher order repeat element consisting, at least in part, of several 39 bp monomers. Such a hierarchical organization of repeats, accompanied by a high degree of polymorphism, has been seen in the case of α satellite DNA (Willard, et al., 1986).

The localization of D1Z2 to the most distal band of the short arm of chromosome 1 raises the possibility that this region might be telomere-associated. Since the resolution of in situ hybridization is several thousand kilobases, one cannot estimate how close D1Z2 is to the actual telomere. However, certain features of D1Z2 resemble those found in other telomere-associated sequences. Thus, telomere associated tandem repeats have been identified in yeast, Drosophila, Xenopus and certain rye grass species (Blackburn and Szostak, *Ann. Rev. Biochem.*, 53:163-194 (1984)). However, in all of these cases, homologous sequences are found at the telomeres of all chromosomes within a species. In humans, a highly polymorphic region is specifically localized at the telomeres of the short arms of the human X and Y chromosomes and is inherited pseudoautosomally (Cook, et al., *Nature*, 317:687-692 (1985)). However, this region differs from D1Z2 in that it lacks complex repeats.

The large number of polymorphic fragments revealed by p1-79 precludes assigning individual bands to specific loci within the hypervariable region. However, studies of nine 3-generation Utah pedigrees show that the genomic regions consisting of sets of allelic fragments at these numerous loci may be inherited as haplotypes; i.e., without recombination. Thus, in 28 informative meioses, no recombination events were detected. Because the actual genetic distance spanned by the hypervariable region and the locations of various polymorphic restriction fragments within this region are unknown, an upper limit to the recombination frequency between loci at opposite ends of D1Z2 cannot be accurately estimated. However, using blots made from pulsed field electrophoretic gels hybridized with probe pYN10.4, which also detects the D1Z2 locus, Nakamura, et al. (1987) have found that unrelated individuals each display one or two polymorphic SfiI fragments ranging in size from ca. 250 to 500 kb and 1-2 polymorphic NotI fragments ranging in size from 450 to 700 kb. Nakamura, et al. have coined the term "midisatellite" to describe this type of chromosome specific repeat.

The foregoing considerations suggest that, despite its complexity, D1Z2, revealed by probe p1-79, may be regarded as a single marker locus useful for mapping genes near the tip of the short arm of human chromosome 1. Because this probe hybridizes strongly and specifically in situ to 1p36.3, it will be useful in cytogenetic applications, such as rapid detection of translocations involving this region, using biotin-labeled probe and fluorescence microscopy. Pinkel, et al., *Nat. Acad. Sci. U.S.A.*, 83:2934-2938 (1986). The highly polymorphic nature of the hypervariable region also makes p1-79 a potentially useful tool for following engraftment of donor bone marrow after transplanation (Blazar, et al., *Blood*, 66:1436-1444 (1985)), and for paternity testing and other forensic applications. Furthermore, an oligomer probe consisting of a single 39 bp repeat unit might be useful in isolating genomic clones capable of revealing additional hypervariable regions. If such additional regions exist, it will be of interest to determine whether they are also located close to chromosomal telomeres.

ATCC Deposit

Probe p1-79 has been deposited with American Type Culture Collection in Rockville, Md., and assigned ATCC accession No. 40323. The deposited probe is a plasmid containing the repeated 39 base sequence described above. In use, the probe would be amplified through bacterial transformation to produce a bacterial colony. The plasmid would then be isoloated and labeled, for example, with radioactive phosphorus.

Having illustrated and described the principles of the invention in a preferred embodiment, it should be apparent to those skilled in the art that the invention can be modified in arrangement and detail without departing from such principles. We claim all modifications coming within the spirit and scope of the following claims.

We claim:

1. A plasmid having ATCC accession No. 40323 which contains a clone of DNA probe p1-79.

2. The probe of claim 1 further comprising a label which enables detection of the probe.

3. A recombinant DNA molecule consisting essentially of a DNA segment containing a sequence which hybridizes to locus D1Z2, a highly polymorphic locus on chromosome 1 in the human genome, the sequence including a sufficient number of bases that, when the molecule is hybridized to polymorphic fragments which are obtained by digesting the D1Z2 locus of a human genome and which are separated by Southern blotting, the resulting blot has a band pattern that is characteristic of the individual from which the genome was taken.

4. The molecule of claim 3 that is a plasmid.

5. The probe of claim 2 wherein the label is a radioactive material.

6. The probe of claim 5 wherein the radioactive material is phosphorus.

7. The molecule of claim 3 further comprising a label which enables detection of the molecule.

8. The molecule of claim 7 wherein the label is a radioactive material.

9. The probe of claim 1 wherein the probe is about 900 base pairs long.

10. The molecule of claim 4 wherein the molecule is about 900 base pairs long.

11. A DNA probe consisting essentially of the DNA sequence CCTGTGTGTGTGCGCGCTGTTCCAGGCTGTCAGATGCTC.

12. A DNA probe consisting essentially of the DNA sequence CCTGGGGGTGCAGAGTGCTGTTCCAGGCTGTCAGAGGCTC.

13. A DNA probe consisting essentially of the DNA sequence CCTGGGGGTGCGGGTGCTGCTCCAGGGTGTCGGAGGCTC.

14. A DNA probe consisting essentially of the DNA sequence CCTGTGGTGTGGGTGCTGTTCCAGGCTGTCAGATCTC.

15. A DNA probe consisting essentially of a sequence of the inserted DNA of the plasmid having ATCC accession No. 40323, which insert hybridizes to locus D1Z2 in the human genome and has a base sequence CCTGGGGGTGNGNGTGCTGTTCCAGGCTGTCAGAGGCTC.

16. The molecule of claim 3 wherein the DNA segment contains a sequence CCTGGGGGTGNGNGTGCTGTTCCAGGCTGTCAGAGGCTC which hybridizes to locus D1Z2 in the human genome.

17. A DNA probe consisting essentially of the DNA sequence CCTGGGGGTGNGNGTGCTGTTCCAGGCTGTCAGAGGCTC.

18. A DNA probe consisting essentially of a sequence of the inserted DNA of a plasmid having ATCC accession No. 40323, which insert hybridizes to the locus D1Z2 of the human genome, the sequence including a sufficient number of bases that, when the probe is hybridized to polymorphic fragments which are obtained by digesting the D1Z2 locus of a human genome and which are separated by Southern blotting, the resulting blot has a band pattern that is characteristic of the individual from which the genome was taken.

19. The probe of claim 18 further comprising a label which enables detection of the probe.

20. The probe of claim 19 wherein the label is a radioactive material.

21. The probe of claim 20 wherein the radioactive material is phosphorus.

22. A recombinant DNA molecule consisting essentially of a DNA segment containing a sequence from the base sequence of probe p1-79 and which hybridizes to locus D1Z2, a highly polymorphic locus on the short arm of chromosome 1 of the human genome, the sequence including a sufficient number of bases that, when the molecule is hybridized to polymorphic fragments which are obtained by digesting the D1Z2 locus of a human genome and separating by Southern blotting, the resulting blot has a band pattern that is characteristic of the individual from which the genome was taken.

23. The molecule of claim 22 that is a plasmid.

24. The probe of claim 22 further comprising a label for detecting the sequence.

25. A DNA probe having a sequence which hybridizes to at least a portion of locus D1Z2, a highly polymorphic locus on the short arm of chromosome 1 of a human genome, and which reveals at least 50 hybridizing fragments when used to probe TagI digested DNA from the D1Z2 locus, the sequence including a sufficient number of bases that, when the probe is hybridized to polymorphic fragments obtained by digesting the D1Z2 locus of a human genome and which are separated by Southern blotting, the resulting blot has a band pattern that is characteristic of the individual from which the genome was taken.

* * * * *

UNITED STATES PATENT AND TRADEMARK OFFICE
CERTIFICATE OF CORRECTION

PATENT NO. : 5,084,566
DATED : January 28, 1992
INVENTOR(S) : Michael Litt et al It is certified that error appears in the above-indentified patent and that said Letters Patent is hereby corrected as shown below:

In the Title: "CHROMOSONE" should be --CHROMOSOME--.

In the References Cited: "Buroker et al., "A hupervariable..." should be --Buroker et al., "A hypervariable...--.

Column 1, line 5, "CHROMOSONE" should be --CHROMOSOME--.
Column 1, line 42, "Nature" should be --Nature--.
Column 2, line 12, "317,687" should be --317:687--.
Column 3, line 66, "useful Botstein" should be --useful. Botstein--.
Column 5, line 47, "8 hours" should be --48 hours--.

Signed and Sealed this

Twelfth Day of October, 1993

*Attest:*

BRUCE LEHMAN

*Attesting Officer*     *Commissioner of Patents and Trademarks*